United States Patent [19]
Kim et al.

[11] Patent Number: 5,767,236
[45] Date of Patent: Jun. 16, 1998

[54] LINEAR THERAPEUTIC PEPTIDES

[75] Inventors: Sun Hyuk Kim, Chestnut Hill; Jacques-Pierre Moreau, Upton, both of Mass.

[73] Assignee: Biomeasure, Inc., Milford, Mass.

[21] Appl. No.: 387,634

[22] Filed: Feb. 13, 1995

Related U.S. Application Data

[63] Continuation-in-part of Ser. No. 929,306, Aug. 13, 1992, abandoned, which is a continuation-in-part of Ser. No. 520,226, May 9, 1990, abandoned.

[51] Int. Cl.$^6$ .............................. C07K 5/00; C07K 7/00; C07K 15/00; A61K 38/00
[52] U.S. Cl. ........................ 530/328; 530/329; 530/345
[58] Field of Search ........................ 530/328, 329, 530/345

[56] References Cited

U.S. PATENT DOCUMENTS

| | | | |
|---|---|---|---|
| 4,207,311 | 6/1980 | Brown et al. | 530/327 |
| 4,331,661 | 5/1982 | Marki et al. | 424/177 |
| 4,650,661 | 3/1987 | Szelke et al. | 424/9 |
| 4,732,890 | 3/1988 | Bonelli et al. | 514/11 |
| 4,737,487 | 4/1988 | Watts et al. | 514/15 |
| 4,803,261 | 2/1989 | Coy et al. | 530/333 |
| 5,084,555 | 1/1992 | Coy et al. | 530/328 |
| 5,100,873 | 3/1992 | Castiglione et al. | 514/15 |

FOREIGN PATENT DOCUMENTS

| | | |
|---|---|---|
| 0109142 | 9/1988 | European Pat. Off. |
| 0345990 | 12/1989 | European Pat. Off. |
| A2231051 | 7/1990 | United Kingdom. |
| 9104040 | 4/1991 | WIPO. |
| 9117181 | 11/1991 | WIPO. |

OTHER PUBLICATIONS

M. Broccardo, et al., "Relative Potency of Bombesin-Like Peptides", Br. J. Pharmacol. vol. 55, pp. 221-227 (1975).

N. Minamino et al., "Neuromedin C. A Bombesin-Like Peptide Identified in Porcine Spinal Cord", Biochemical and Biophysical Research Communications, vol. 119, No. 1, pp. 14-20 (1984).

L.H. Wang et al., "des-met Carboxyl-terminally Modified Analogues of Bombesin Function as Potent Bombesin Receptor Antagonists . . . ", Jour. of Biol. Chem., vol. 265, No. 26, pp. 15695-157036 (1990).

Rudinger, Peptide Hormones, Parsons (Ed.), U Park Press, Baltimore, pp. 1-7 (1976).

Lehninger, Principles of Biochemistry, Anderson et al. (Eds), Worth Publisher, Inc., New York, pp. 95-117, (1982).

Cram et al., Organic Chemistry, 2nd Edition, McGraw-Hill Book Company, New York, pp. 607-613 (1964).

Cuttitta et al., "Autocrine Growth Factors in Human Small Cell Lung Cancer," Cancer Surveys 4:707-727 (1985).

Zachary et al., "High-Affinity Receptors For Peptides Of The Bombesin Family In Swiss 3I3 Cells", Proc. Natl. Acad. Sci. (USA) 82:7616-7620 (1985).

Heinz-Erian et al., "[D-Phe$^{12}$] Bombesin Analogues:A New Class Of Bombesin Receptor Antagonists", Am. J. of Physiol., G439-G442 (1987).

Martinez et al., J. Med. Chem., "Synthesis and Biological Activities of Some Pseudo-peptide Analogues of Tetragastrin: The Importance of the Peptide Backbone," 28:1874-1879 (1985).

Sasaki et al., J. Med. Chem., "Solid-phase Synthesis and Biological Properties of ψ [CH$_2$NH] Pseudopeptide Analogues of a Highly Potent Somatostatin Octapeptide," 30:1162-1166 (1987).

Rodriquez et al., J. Med. Chem., "Synthesis and Biological Activities of the C-terminal heptapeptide of cholacystokinin. On the importance of the Peptide Bonds," 30:1366-1373 (1987).

Gargosky et al., Biochem. J., "C-Terminal Bobesin Sequence Requirements for Binding and effects on Protein Synthesis in Swiss 3T3 cells," 247:427-432 (19.

Coy et al., "Progress in the development of competitive bombesin antagonists", in Abstract of the Intl. Sym. on Bombesin-Like Peptides in Health and Disease, Rome, p. 105 (Oct. 1987).

Rivier et al., "Competitive Antagonists of Peptide Hormones," in Abstract of the Intl. Sym. on Bombesin-Like Peptides in Health and Disease, Rome, p. 135 (Oct. 1987).

Dubreuil et al., "Degradation of a tetragastrin analogue by a membrane fraction from rat gastric mucosa," Drug Design and Delivery 2:49-54, 1987.

(List continued on next page.)

*Primary Examiner*—Avis M. Davenport
*Attorney, Agent, or Firm*—Fish & Richardson P.C.

[57] ABSTRACT

The invention features linear therapeutic peptides of the following formula:

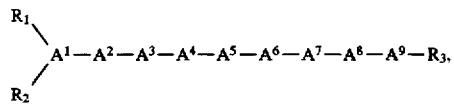

in which $A^1$ is a D-α-aromatic amino acid or a D-α-tethered amino acid; $A^2$ is Gln, His, 1-methyl-His, or 3-methyl-His; $A^3$ is the D- or L-isomer selected from Nal, Trp, Phe, and p-X-Phe, where X is F, Cl, Br, NO$_2$, OH or CH$_3$; $A^4$ is Ala, Val, Leu, Ile, Nle, or α-aminobutyric acid; $A^5$ is Val, Ala, Leu, Ile, Nle, Thr, or α-aminobutyric acid; $A^6$ is Gly, Sar, β-Ala, or the D-isomer selected from Ala, N-methyl-Ala, Trp, and Nal; $A^7$ is His, 1-methyl-His, 3-methyl-His, Lys, or ε-alkyl-Lys; $A^8$ is Leu, Ile, Val, Nle, α-aminobutyric acid, Trp, Pro, Nal, Chx-Ala, Phe, or p-X-Phe, where X is F, Cl, Br, NO$_2$, OH or CH$_3$; $A^9$ is Met, Met-oxide, Leu, Ile, Nle, α-aminobutyric acid, or Cys; each $R_1$ and $R_2$, independently, is H, $C_{1-12}$ alkyl, $C_{7-10}$ phenylalkyl, or COE$_1$, where E$_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is COE$_1$, the other must be H; and $R_3$ is OH, NH$_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, $C_{11-20}$ naphthylalkylamino; or a pharmaceutically acceptable salt of such peptides.

26 Claims, 2 Drawing Sheets

OTHER PUBLICATIONS

Sawyer et al., J. Med. Chem. Design, Structure–Activity, and Molecular Modeling Studies of Patent Renin Inhibitory Peptides having N–terminal $N^{in}$ for Trp (FTR) 31: 18–30, 1988.

Nagadin et al., Peptides, "In Vivo Activities of Peptide and Pseudo–Peptide Analogs of the C–Terminal Octapeptide of Cholesystokinin on Pancreatic Secretion in the rat," 8:1023–1028 (1987).

Martinez et al., "Selective Cholecystokinin Receptor Antagonists," in Cholecystokinin Antagonists 29–51, Alan R. Liss, Inc., (1988).

Coy et al., Tetrahedron, "Solid Phase Reductive Alkylation Techniques in Analogue Peptide Bond and Side chain Modification" 44:835–841 (1988).

Heikkila et al., J. ofUBiol. Chem., "Bombesin–related Peptides Induce Calcium Mobilization in a Subset of Human Small Cell Lung Cancer Cell Lines" 262:16456–16460 (1987).

Vander Elst et al., J. Peptide Protein Res. 27:633 (1986).

Spatola et al., Tetrahedron, Amide Bond Surrogates: Pseudopeptides and Macrocycles 44:821–833 (1988).

Aumelas et al., Int. J. Peptide Protein Res. 30:596 (1987).

Bardi et al. Tetrahedron 44:761 (1988).

Alexander et al. Cancer Res. 48:1439 (1988).

Coy et al., J. Biol. Chem. 263:5056 (1988).

Rossowski et al. Abstract, The Endocrine Society (1988).

Sawyer et al. Tetrahedron 44:661 (1988).

Leij et al., Abstract Ned. Tijd. Geneek (May 28, 1988).

Rivier et al., Biochem. 17:1766 (1978).

Woll et al., BBRC 155:359 (Aug. 1988).

Plevin et al., Trends in Pharm. Sci. 9:387 (1988).

Trepel et al., BBRC 156:1383 (Nov. 15, 1989).

Dickinson et al. BBRC 157:1154 (Dec. 30, 1988).

Mahmoud et al., Small Cell Lung Cancer Bombesin Receptors are Antagonized by Reduced Peptide Bond Analogues, Life Sciences, 44:367 (1989).

Hocart et al., Analogues of Growth Hormone–Releasing Factor (1–29) Amide Containing the Reduced Peptide Bond Isostere in the N–terminal Region, J. Med. Chem. 33:1954 (1990).

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:

```
        ( A ) LENGTH: 9
        ( B ) TYPE: amino acid
        ( C ) STRANDEDNESS: Not Relevant
        ( D ) TOPOLOGY: Not Relevant ( i x ) FEATURE:
        ( D ) OTHER INFORMATION:
            The sequence contains at position 1 a pyroglutamate,
            rather than a glutamate, and has an amide C-terminus
            ( i . e . ,  COOH ).

( x i ) SEQUENCE DESCRIPTION: SEQ ID NO: 1:

Glu  Gln  Trp  Ala  Val  Gly  His  Phe  Met
                        5

( 2 ) INFORMATION FOR SEQ ID NO: 2:

( i ) SEQUENCE CHARACTERISTICS:
        ( A ) LENGTH: 9
        ( B ) TYPE: amino acid
        ( C ) STRANDEDNESS: Not Relevant
        ( D ) TOPOLOGY: Not Relevant ( i x ) FEATURE:
        ( D ) OTHER INFORMATION:
            The sequence contains at position 1 a pyroglutamate,
            rather than a glutamate, and has an amide C-terminus
            ( i . e . ,  COOH ).

( x i ) SEQUENCE DESCRIPTION: SEQ ID NO: 2:

Glu  Gln  Trp  Ala  Val  Gly  His  Leu  Leu
                        5

( 2 ) INFORMATION FOR SEQ ID NO: 3:

( i ) SEQUENCE CHARACTERISTICS:
        ( A ) LENGTH: 8
        ( B ) TYPE: amino acid
        ( C ) STRANDEDNESS: Not Relevant
        ( D ) TOPOLOGY: Not Relevant ( i x ) FEATURE:
        ( D ) OTHER INFORMATION:
            The sequence contains at position 1 an acetylated His,
            rather than a His, and has an amide C-terminus (i.e.,
            COOH).

( x i ) SEQUENCE DESCRIPTION: SEQ ID NO: 3:

His  Trp  Ala  Val  Gly  His  Leu  Leu
                   5
```

LINEAR THERAPEUTIC PEPTIDES

CROSS REFERENCE TO RELATED APPLICATIONS

This invention is a continuation-in-part of application Ser. No. 07/929,306, filed Aug. 13, 1992, now abandoned which is a continuation-in-part of application Ser. No. 07/520,226, filed May 9, 1990, now abandoned.

BACKGROUND OF THE INVENTION

This invention relates to peptides useful for treatment of benign or malignant proliferation of tissue.

The amphibian peptide bombesin (see Anastasi et al., Experientia 27:166–167, 1971) is closely related to the mammalian gastrin-releasing peptides ("GRP"), e.g., porcine GRP (McDonald et al., Biochem. Biophys. Res. Commun. 90:227–233, 1979) and human GRP. Bombesin has been found to be a growth factor for a number of human cancer cell lines, including small-cell lung carcinoma ("SCLC"), and has been detected in human breast and prostate cancer. Haveman et al., eds. *Recent Results in Cancer Research—Peptide Hormones in Lung Cancer*, Springer-Verlag, N.Y., 1986. A number of these cancers are known to secrete peptide hormones related to GRP or bombesin. Consequently, antagonists to bombesin have been proposed as agents for the treatment of these cancers.

Cuttitta et al. demonstrated that a specific monoclonal antibody to bombesin inhibited in vivo the growth of a human small-cell lung cancer cell line xenografted to nude mice. Cuttitta et al., Cancer Survey 4:707–727, 1985. In 3T3 murine fibroblasts which are responsive to the mitotic effect of bombesin, Zachary and Rozengurt observed that a substance P antagonist, Spantide, acted as a bombesin antagonist. Zachary et al., Proc. Natl. Acad. Sci. (USA), 82:7616–7620, 1985. Heinz-Erian et al. replaced His at position 12 in bombesin with D-Phe and observed bombesin antagonist activity in dispersed acini from guinea pig pancreas. Heinz-Erian et al., Am. J. of Physiol. 252:G439-G442, 1987. Rivier reported work directed toward restricting the conformational freedom of the bioactive C-terminal decapeptide of bombesin by incorporating intramolecular disulfide bridges; however, Rivier mentioned that, so far, bombesin analogs with this modification fail to exhibit any antagonist activity. Rivier et al., "Competitive Antagonists of Peptide Hormones," in Abstracts of the International Symposium on Bombesin-Like Peptides in Health and Disease, Rome, Italy October, 1987.

Bombesin exhibits both direct and indirect effects on the gastrointestinal tract, including the release of hormones and the stimulation of pancreatic, gastric, and intestinal secretion and of intestinal mobility. GRP and cholecystokinin, which are released by bombesin, have been shown to play a role in the maintenance of normal gastrointestinal mucosa as well as in augmenting growth of normal and neoplastic tissues. The growth of xenografted human colon and stomach carcinomas in nude mice has been stimulated by the administration of gastrin and later inhibited with the addition of secretin (Tanake et al., Tokaku J. Exp. Med. 148:459, 1986) and the growth of MC-26 murine colon carcinoma which possesses gastrin receptors is stimulated by pentagastrin (Winsett et al., Surgery 99:302 1980), and inhibited by proglumide, a gastrin-receptor antagonist (Beauchamp et al., Ann. Surg. 202:303, 1985). Bombesin has been found to act concurrently as both a trophic agent for normal host pancreas and a growth inhibitory agent in xenografted human pancreatic tumor tissue. Alexander et al., Pancreas 3:247, 1988.

SUMMARY OF THE INVENTION

Abbreviations:
Chx-Ala=cyclohexyl-Ala (3-cyclohexylalanine)
pGlu=pyroglutamic acid
Nle=norleucine
D-Cpa=D-p-chlorophenylalanine
HyPro=hydroxyproline
Nal=3-(α-naphthyl)-alanine, or 3- (β-naphthyl)-alanine
DOPA=3,4-dihydroxyphenylalanine
Tcc=1, 2, 3, 4-tetrahydro-2-carboline-3-carboxylic acid
Tic=1, 2, 3, 4-tetrahydroisoquinoline-3-carboxylic acid
Aza-Tyrosine=3- (5-hydroxy-2-pyridyl) -alanine
Sar=sarcosine
1- or 3-methyl-His=His with a methyl group on its position 1 or 3 heterocyclic nitrogen
ε-alkyl-Lys=Lys with its NE substituted by an alkyl group The invention features linear therapeutic peptides of the following formula:

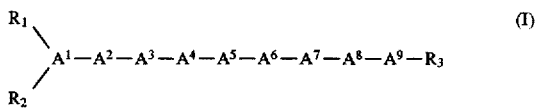

in which:
$A^1$ is a D-α-aromatic amino acid or a D-α-tethered amino acid; R is delated
$A^2$ is Gln, His, 1-methyl-His, or 3-methyl-His;
$A^3$ is the D- or L-isomer selected from Nal, Trp, Phe, and p-X-Phe, where X is F, Cl, Br, $NO_2$, OH or $CH_3$;
$A^4$ is Ala, Val, Leu, Ile, Nle, or α-aminobutyric acid;
$A^5$ is Val, Ala, Leu, Ile, Nle, Thr, or α-aminobutyric acid;
$A^6$ is Gly, Sar, P-Ala, or the D-isomer selected from Ala, N-methyl-Ala, Trp, and Nal;
$A^7$ is His, 1-methyl-His, 3-methyl-His, Lys, or ε-alkyl-Lys;
$A^8$ is Leu, Ile, Val, Nle, a-aminobutyric acid, Trp, Pro, Nal, Chx-Ala, Phe, or p-X-Phe, where X is F, Cl, Br, $NO_2$, OH or $CH_3$;
$A^9$ is Met, Met-oxide, Leu, Ile, Nle, α-aminobutyric acid, or Cys;
each $R_1$ and $R_2$, independently, is H, $C_{1-12}$ alkyl, $C_{7-10}$ phenylalkyl, or $COE_1$, where $E_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is $COE_1$, the other must be H; and
$R_3$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, $C_{11-20}$ naphthylalkylamino; or a pharmaceutically acceptable salt of such peptides.

What is meant by "aromatic α-amino acid" is an amino acid residue of the formula

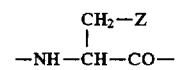

where Z is a moiety containing an aromatic ring. Examples of Z include, but are not limited to, the following structures with or without a substituent X on the aromatic ring (where X is halogen, $NO_2$, $CH_3$, or OH):

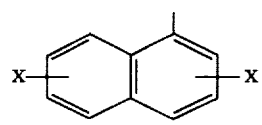

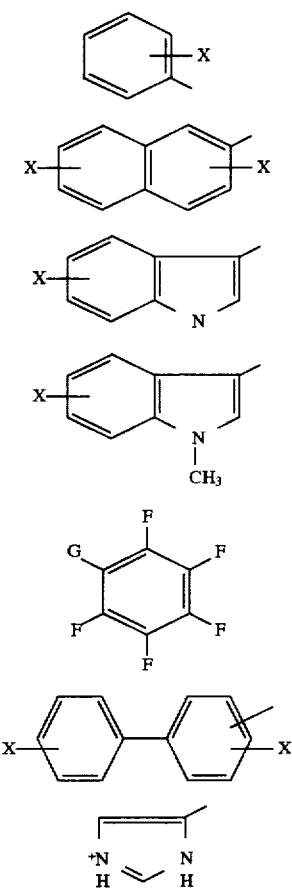

What is meant by "tethered α-amino acid" is an α-amino acid with a carbon atom of its side chain tethered to the N atom of the α-amino group. Examples include, but are not limited to, Pro, HyPro, Tic, and Tcc.

The symbol $A^1$, $A^2$, or the like herein stands for the residue of an α-amino acid. Except for tethered amino acids (e.g., Pro, HyPro, Tcc, or Tic) and Sar, such symbols represent the general structure, —NH—CH(R)—CO— or =N—CH(R)—CO— when it is at the N-terminus or —NH—CH(R)—CO— when it is not at the N-terminus, where R denotes the side chain (or identifying group) of the α-amino acid, e.g., R is —CH$_2$COOH for Asp. Note that the N-terminus is at the left and the C-terminus at the right in accordance with the conventional representation of a polypeptide chain. When $A^6$ is Sar, it has the structure of —N(CH$_3$)—CH$_2$—CO—. The residue of a tethered amino acid, on the other hand, is of the structure —N—CH(R)—CO—, where N, C and R together form a ring. HyPro herein refers to any of 2-hydroxy-Pro, 3-hydroxy-Pro, 4-hydroxy-Pro, and 5-hydroxy-Pro; 4-hydroxy-Pro is preferred.

Furthermore, where the amino acid residue is optically active, it is the L-form configuration that is intended unless the D-form is expressly designated. An alkyl group, if not specified, contains 1–12 carbon atoms. COE$_1$ stands for

C—E$_1$.

In formula (I) given above, when either of R$_1$ or R$_2$ is an aliphatic, aromatic, or lipophilic group, the in vivo activity can be long lasting, and delivery of the compounds of the invention to the target tissue can be facilitated.

Preferably, in formula (I), $A^1$ is the D-isomer selected from Nal, DOPA, Trp, Tcc, Tic, Aza-Tyr, Phe, and p-X-Phe, where X is F, Cl, Br, NO$_2$, OH or CH$_3$ or is deleted. It is particularly preferred that $A^1$ be the D-isomer selected from Phe and p-X-Phe, where X is F, Cl, Br, NO$_2$, OH or CH$_3$; $A^7$ be His, 1-methyl-His, or 3-methyl-His; $A^8$ be Leu, Ile, Val, Nle, α-aminobutyric acid, Trp, Nal, Chx-Ala, Phe, or p-X-Phe, where X is F, Cl, Br, NO$_2$, OH or CH$_3$; and E$_1$ be C$_{1-20}$ alkyl, C$_{3-20}$ alkenyl, C$_{3-20}$ alkynyl, phenyl, naphthyl, or C$_{7-10}$ phenylalkyl.

Also preferably, in formula (I), $A^2$ is His, 1-methyl-His, or 3-methyl-His; or $A^9$ is Leu, Ile, Nle, α-aminobutyric acid, or Cys. Other preferred peptides of formula (I) are those in which $A^1$ is D-Phe, D-Cpa, D-DOPA, or is deleted; $A^2$ is Gln, His, 1-methyl-His, or 3-methyl-His; $A^3$ is Trp; $A^4$ is Ala; $A^5$ is Val; $A^6$ is Sar, Gly, D-Phe, or D-Ala; $A^7$ is His; $A^8$ is Leu, Phe, Chx-Ala, or Cys; and $A^9$ is Met, Leu, Ile, Nle, or Cys.

Particularly preferred peptides of the invention include the following:

H-D-Phe-Gln-Trp-Ala-Val-Gly-His-Leu-Leu-NH$_2$;
H-D-Phe-Gln-Trp-Ala-Val-Gly-His-Leu-Met-NH$_2$;
H-D-Cpa-Gln-Trp-Ala-Val-Gly-His-Leu-Met-NH$_2$;
H-D-Cpa-Gln-Trp-Ala-Val-Gly-His-Leu-Leu-NH$_2$;
H-D-Phe-Gln-Trp-Ala-Val-D-Ala-His-Leu-Leu-NH$_2$;
H-D-Phe-Gln-Trp-Ala-Val-D-Ala-His-Leu-Met-NH$_2$;
H-D-Cpa-Gln-Trp-Ala-Val-D-Ala-His-Leu-Met-NH$_2$;
H-D-Phe-Gln-Trp-Ala-Val-Gly-His-Phe-Leu-NH$_2$;
H-D-Phe-Gln-Trp-Ala-Val-D-Ala-His-Phe-Met-NH$_2$;
H-D-Phe-Gln-Trp-Ala-Val-D-Ala-His-Phe-Leu-NH$_2$;
H-D-Phe-Gln-Trp-Ala-Val-Gly-His-Leu-Nle-NH$_2$;
H-D-Phe-Gln-Trp-Ala-Val-D-Ala-His-Leu-Nle-NH$_2$;
H-D-Phe-Gln-Trp-Ala-Val-Gly-His-Phe-Nle-NH$_2$;
H-D-Phe-Gln-Trp-Ala-Val-D-Ala-His-Phe-Nle-NH$_2$;
Acetyl-His-Trp-Ala-Val-D-Ala-His-Leu-Leu-NH$_2$;
H-D-Phe-Gln-Trp-Ala-Val-Gly-His-Chx-Ala-Leu-NH$_2$;
H-D-Phe-Gln-Trp-Ala-Val-Gly-His-Phe-Met-NH$_2$;
H-D-Tyr-Gln-Trp-Ala-Val-Gly-His-Phe-Met-NH$_2$;
H-D-Tyr-Gln-Trp-Ala-Val-Gly-His-Leu-Leu-NH$_2$;
H-D-Tyr-Gln-Trp-Ala-Val-Gly-His-Leu-Met-NH$_2$;
H-D-Tyr-Gln-Trp-Ala-Val-Gly-His-Phe-Nle-NH$_2$;
H-D-Tyr-Gln-Trp-Ala-Val-Gly-His-Leu-Nle-NH$_2$;
H-D-Tyr-Gln-Trp-Ala-Val-Gly-His-Phe-Leu-NH$_2$;
Propionyl-His-Trp-Ala-Val-D-Ala-His-Leu-Leu-NH$_2$;
Acetyl-His-Trp-Ala-Val-Gly-His-Leu-Leu-NH$_2$ (SEQ ID NO:3).
H-D-DOPA-Gln-Trp-Ala-Val-Gly-His-Leu-Leu-NH$_2$, and
H-D-DOPA-Gln-Trp-Ala-Val-Gly-His-Phe-Nle-NH$_2$.

Analogs of the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluene sulfonic, trifluoroacetic, or pamoic acid, as well as polymeric acids such as tannic acid or carboxymethyl cellulose, and salts with inorganic acids such as the hydrohalic acids, e.g., hydrochloric acid, sulfuric acid or phosphoric acid.

Other features and advantages of the invention will be apparent from the following description of the preferred embodiments thereof, and from the claims.

BRIEF DESCRIPTION OF THE DRAWINGS

The drawings will be first described.

DESCRIPTION OF THE PREFERRED EMBODIMENTS

Figure 1:
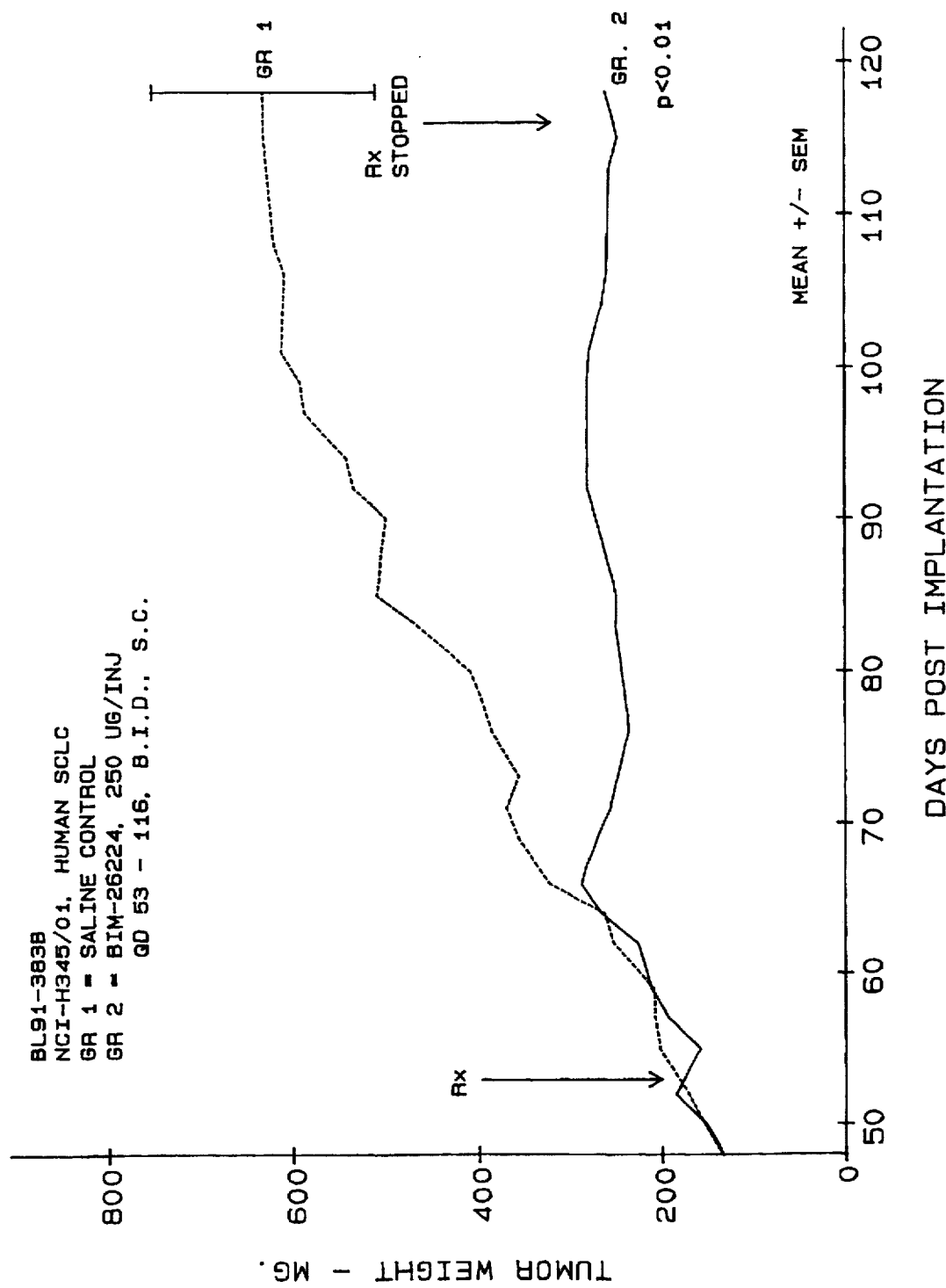
FIGS. 1 and 2 are graphs showing the growth inhibitory effect of two compounds of the present invention on small cell lung carcinoma and non-small cell lung carcinoma.

We now describe the structure, synthesis, activities, and use of the preferred embodiments of the present invention.

STRUCTURE

Peptides of the invention are derived from litorin, neuromedin B, neuromedin C, bombesin (last ten amino acids) and human GRP (last ten amino acids). Bombesin, neuromedin B, neuromedin C, litorin, and GRP analogs of the invention are described in Coy et al., U.S. patent application Ser. No. 502,438, filed Mar. 30, 1990, which is a continuation-in-part of U.S. patent application Ser. No. 397,169, filed Aug. 21, 1989, which is a continuation-in-part of U.S. patent application Ser. No. 376,555, filed Jul. 7, 1989, and U.S. patent application Ser. No. 394,727, filed Aug. 16, 1989, both of which are continuation-in-parts of U.S. patent application Ser. No. 317,941, filed Mar. 2, 1989, which is a continuation-in-part of U.S. patent application Ser. No. 282,328, filed Dec. 9, 1988, which in turn is a continuation-in-part of U.S. patent application Ser. No. 257,998, filed Oct. 14, 1988, which in turn is a continuation-in-part of U.S. patent application Ser. No. 248,771, filed Sep. 23, 1988, which in turn is a continuation-in-part of Coy et al., U.S. patent application Ser. No. 207,759, filed Jun. 16, 1988, which in turn is a continuation-in-part of Coy et al., U.S. patent application Ser. No. 204,171, filed Jun. 8, 1988, which in turn is a continuation-in-part of Coy et al., U.S. patent application Ser. No. 173,311, filed Mar. 25, 1988, which in turn is a continuation-in-part of Coy et al. U.S. patent application Ser. No. 100,571, filed Sep. 24, 1987; all of which are assigned to the same assignee and hereby incorporated by reference; or as described in Zachary et al., Proc. Nat. Aca. Sci. 82:7616, 1985; Heimbrook et al., "Synthetic Peptides: Approaches to Biological Problems", UCLA Symposium on Mol. and Cell. Biol. New Series, Vol. 86. ed. Tam and Kaiser; Heinz-Erian et al., Am. J. Physiol. G439, 1986; Martinez et al., J. Med. Chem. 28:1874, 1985; Gargosky et al., Biochem. J. 247:427, 1987; Dubreuil et al., Drug Design and Delivery, Vol 2:49, Harwood Academic Publishers, GB, 1987; Heikkila et al., J. Biol. Chem. 262:16456, 1987; Caranikas et al., J. Med. Chem. 25:1313, 1982; Saeed et al., 1989, Peptides 10:597; Rosell et al., Trends in Pharmacological Sciences 3:211, 1982; Lundberg et al., Proc. Nat. Aca. Sci. 80:1120, 1983; Engberg et al., Nature 293:222, 1984; Mizrahi et al., Euro. J. Pharma. 82:101, 1982; Leander et al., Nature 294:467, 1981; Woll et al., Biochem. Biophys. Res. Comm. 155:359, 1988; Rivier et al., Biochem. 17:1766, 1978; Cuttitta et al., Cancer Surveys 4:707, 1985; Aumelas et al., Int. J. Peptide Res. 30:596, 1987; all of which are hereby incorporated by reference.

Synthesis of Analogs

The synthesis of one of the compounds of the invention, BIM-26187 (i.e., D-Phe-Gln-Trp-Ala-Val-Gly-His-Leu-Leu-NH$_2$), follows.

1) Incorporation of α-t-butoxycarbonyl ("BOC")-leucine on 4-methyl benzhydrylamine.

4-methyl benzhydrylamine-polystyrene resin (Bachem, Inc.) (0.72 meq/g) in the chloride ion form is placed in the reaction vessel of an ACT200 peptide synthesizer (Advanced Chem Tech, Inc.) programmed to perform the following reaction cycle: (a) methylene chloride; (b) 10% triethylamine in chloroform; (c) methylene chloride; and (d) dimethylformide.

The neutralized resin is mixed with BOC-leucine and diisopropylcarbodiimide (3 molar eq each) in methylene chloride for 1 hour. The resulting amino acid resin is washed on the synthesizer with dimethylformamide and treated with 5% acetic anhydride in dimethylformamide for 5 min. Then it is washed with dimethylformamide and methylene chloride.

2) Couplings of the remaining amino acids.

The peptide synthesizer is programmed to perform the following reaction cycle: (a) methylene chloride; (b) 33% trifluoroacetic acid ("TFA") in methylene chloride (2 times for 5 and 25 min. each); (c) methylene chloride; (d) isopropyl alcohol; (e) 10% triethylamine in chloroform; and (f) methylene chloride.

The following amino acids (3 molar eq.) are then coupled successively by the same procedure: BOC-Leu, BOC-His (tosyl), BOC-Gly, BOC-Val, BOC-Ala, BOC-Trp, BOC-Gln (coupled in the presence of 1 eq. hydroxybenzotriazole), BOC-D-Phe (coupled in the presence of 1 eq. hydroxybenzotriazole). The completed resin is then washed with methanol and air dried.

The peptide resin described above (1.41 g) is mixed with anisole (5 ml), dithiothreitol (50 mg), and anhydrous hydrogen fluoride (25 ml) at 0° C. for one hour. Excess hydrogen fluoride is evaporated rapidly under a stream of dry nitrogen, and the residue is washed in ether. Crude peptide is dissolved in 100 ml of 4M acetic acid and the solution is then evaporated under reduced pressure. The crude peptide is dissolved in minimum volume of methanol/water and triturated with ethyl acetate. The triturated peptide is applied to a column (9.4 mm I.D.×50 cm) of octadecylcilane-silica (WHATMAN PARTISIL 10 ODS -2M9). The peptide is eluted with a linear gradient of 20–80% of 50/50 0.1% TFA/Acetronitrile i 0.1% TFA in water. Fractions are examined by analytical high performance liquid chromatography and appropriate fractions are evaporated to a small volume, which is further lyophilized, gives 65 mg of the product as a colorless powder.

Other compounds of the present invention, e.g., BIM-26224 (i.e., H-D-Phe-Gln-Trp-Ala-Val-Gly-His-Phe-Nle-NH$_2$), can be prepared in an analogous manner by making appropriate modifications of the above-described synthetic method.

ACTIVITIES (1) Assay on binding to GRP receptor

Procedures

Cell Culture

Rat AR42J pancreatic acinar cells were cultured in Dulbecco's modified Eagle's medium without antibiotics and supplemented with 10% (vol/vol) fetal calf serum. The incubation atmosphere consisted of 10% C)$_2$-90% humidified air at 37° C.

Receptor Binding Assay

Membranes for the bombesin receptor binding assay were obtained by homogenizing AR42J cells (Polytron, setting 6, 15 sec) in ice-cold 50 mM Tris-HCl (Buffer A) and centrifuging twice at 39,000× g (10 min), with an intermediate resuspension in fresh buffer. The final pellets were resuspended in 50 mM Tris-HCl, containing 0.1 mg/ml bacitracin, and 0.1% BSA (Buffer B), and held on ice for the receptor binding assay.

For assay, aliquots (0.4 ml) were incubated with 0.05 ml [$^{125}$I-Tyr$^4$] bombesin (~2200 Ci/mmol, New England Nuclear) and Buffer B, with and without 0.05 ml of unlabeled competing analogs. After a 30 min incubation (4° C.), the bound [$^{125}$I-Tyr$^4$] bombesin was separated from the free by rapid filtration through GF/B filters which had been previously soaked in 0.1% polyethyleneimine. The filters were then washed three times with 5 ml aliquots of ice-cold Buffer A. Specific binding was defined as the total [$^{125}$I-Tyr$^4$] bombesin bound minus that bound in the presence of 1 μM unlabeled bombesin.

Results

The results (expressed as IC$^{50}$ in nm) and the structures of the tested compounds are shown in Table 1. Replacement of p-Glu at position A$^1$ in a prior art compound (i.e., litorin or Leu-litorin) with an aromatic amino acid led unexpectedly to a great increase in their affinity for the GRP receptor. For example, replacement of p-Glu with D-Tyr resulted in a 5- to 15-time increase in the affinity (compare litorin with BIM-26271, or Leu-litorin with BIM-26278). Modification at position A$^8$ or A$^9$ or both further increases the affinity. Thus, BIM-26270 has an IC$_{50}$ being as low as 0.1 nm, compared to 2.4 nm for litorin or 23 nm for Leu-litorin—an increase of 24 to 230 times in the affinity for the GRP receptors.

amino acid at its N-terminus, are capable of inhibiting the growth of different human and animal tumors. Note that the percent/control value is as low as 31% in treating colon tumor with BIM-26187, which, as shown in Table 1 above, possess a much greater affinity for the GRP receptor compared to Leu-litorin.

The structural formulae of BIM-26187, BIM-26218, BIM-26247, and BIM-26225 are as follows:

BIM-26187
H-D-Phe-Gln-Trp-Ala-Val-Gly-His-Leu-Leu-NH$_2$;
BIM-26218
H-D-Phe-Gln-Trp-Ala-Val-Gly-His-Leu-Met-NH$_2$;
BIM-26247
Propionyl-His-Trp-Ala-Val-D-Ala-His-Leu-Leu-NH$_2$
BIM-26225
Acetyl-His-Trp-Ala-Val-Gly-His-Leu-Leu-NH$_2$ (SEQ ID NO:3)

TABLE 1

AFFINITY BINDING DATA FOR THE GRP RECEPTORS OF LINEAR BOMBESIN ANALOGS WITH AROMATIC AMINO ACID REPLACEMENT IN POSITION A$^1$*

| Code Name | Structure | IC$_{50}$ (nm) |
|---|---|---|
| Litorin | p-Glu—Gln—Trp—Ala—Val—Gly—His—Phe—Met—NH$_2$ (SEQ ID NO:1) | 2.4 |
| BIM-26269 | H—D-Phe—Gln—Trp—Ala—Val—Gly—His—Phe—Met—NH$_2$ | 1.4 |
| BIM-26271 | H—D-Tyr—Gln—Trp—Ala—Val—Gly—His—Phe—Met—NH$_2$ | 0.5 |
| Leu-Litorin | p-Glu—Gln—Trp—Ala—Val—Gly—His—Leu—Leu—NH$_2$ (SEQ ID NO:2) | 23 |
| BIM-26187 | H—D-Phe—Gln—Trp—Ala—Val—Gly—His—Leu—Leu—NH$_2$ | 5.0 |
| BIM-26278 | H—D-Tyr—Gln—Trp—Ala—Val—Gly—His—Leu—Leu—NH$_2$ | 1.5 |
| BIM-26224 | H—D-Phe—Gln—Trp—Ala—Val—Gly—His—Phe—Nle—NH$_2$ | 0.7 |
| BIM-26274 | H—D-Tyr—Gln—Trp—Ala—Val—Gly—His—Leu—Met—NH$_2$ | 0.3 |
| BIM-26270 | H—D-Tyr—Gln—Trp—Ala—Val—Gly—His—Phe—Nle—NH$_2$ | 0.1 |
| BIM-26279 | H—D-Tyr—Gln—Trp—Ala—Val—Gly—His—Leu—Nle—NH$_2$ | 1.7 |
| BIM-26288 | H—D-Tyr—Gln—Trp—Ala—Val—Gly—His—Phe—Leu—NH$_2$ | 0.7 |

*See formula (I) in "SUMMARY OF THE INVENTION" above.

(2) Assay on inhibition of tumor growth

Procedures

Subcutaneous Tumor Assays

Treatment of tumors induced by subcutaneous implantation of in vitro maintained cell cultures was initiated only when well established as progressively growing tumors in the first transplant generation from in vitro culture. "No takes" were culled and animals with tumors of similar size were carefully randomized into control and test groups.

Analogues were tested against all tumor systems except SCLC's and NSCLC's at a screening dose of 100 μg/injection, s.c., in the flank opposite from the tumor, b.i.d. Lung tumors (SCLC and NSCLC) were tested at 250 μg/injection, s.c., b.i.d. Rat breast tumors were tested at 400 Ag/injection, s.c., b.i.d., an equivalent extrapolation from the mouse dose.

In vivo transplantation established tumor systems were implanted s.c. as a 1–2 mm$^3$ mince of tumor tissue. Treatment was initiated within 2 to 3 days of implantation.

Measurement of Tumor Growth

Tumor weights (mgs) from tumor dimensions (mm×mm) were calculated following the formula of a prolate ellipsoid: L×W$^2$/2, where L is the longer of the two measurements.

Tumor measurements were determined with a vernier caliper three times/week.

Results

As shown in Table 3, BIM-26187, BIM-26218, BIM-26247 and BIM-26225, all of which contain an aromatic Thirteen different tumor models were used to evaluate and screen the compounds. Details regarding these tumors are shown in Table 2.

TABLE 2

HUMAN AND ANIMAL TUMOR TEST SYSTEMS

Tumor Designation

Prostate Tumors

| | |
|---|---|
| AT-3 | Androgen resistant, undifferentiated fast growing carcinoma of the rat prostate. A subline of R-3327-H. Tested as subcutaneous xenografts in athymic nudes. |
| 11095 | Androgen insensitive, squamous cell carcinoma of the rat prostate. Originating and transplantable in Fischer 344 strain rats. Tested as subcutaneous xenografts in athymic nudes. |
| 2PR121D/R | Androgen resistant, poorly differentiated adenocarcinoma of the rate prostate derived as an androgen resistant subline of 2PR121D(1)/S. Tested as subcutaneous tumors in Nb strain rats. |

Breast Tumors

| | |
|---|---|
| MX-1 | Estrogen independent, human poorly differentiated mammary carcinoma. Tested as subcutaneous xenografts in athymic |

TABLE 2-continued

HUMAN AND ANIMAL TUMOR TEST SYSTEMS

| Tumor Designation | |
|---|---|
| | nude females. |
| R3230Ac | Estrogen sensitive (not dependent) rat mammary tumor transplantable in Fischer 344 strain rats. |
| 13762NF | Estrogen insensitive rat mammary tumor transplantable in Fischer 344 strain rats. |
| Colon Tumors | |
| CZ-1 | Mucinous adenocarcinoma, human, tested as xenografts in athymic nude females. |
| GOB-G | Moderately differentiated adenocarcinoma, human, tested as xenografts in athymic nude females. |
| Hepatoma (Liver) | |
| M5123 | Hepatoma, rat |
| M7777 | Hepatoma, rat |
| M7906 | Hepatoma, rat |
| Lung Tumors | |
| NCI-H345 | An in vitro maintained human small cell lung cancer (SCLC) graciously prided by Dr. A. Gazdar. Cell agglomerates produce slow, progressively growing tumors in approximately 80% of athymic nude mice when implanted subcutaneously. Tested as well established subcutaneous xenografts in athymic nudes. |
| A-549 | An in vitro maintained human non-small cell lung cancer (NSCLC) obtained from the American Type Culture Collection repository. Implanted s.c. as a cell suspension and resultant tumors treated when tumors were of palpable size. |

TABLE 3

Response of Human and Animal Tumors to Treatment with Bombesin/Gastrin Releasing Peptide Analogues (Percent Test/Control\*)

| | BIM-26187 | BIM-26218 | BIM-26247 | BIM-26225 |
|---|---|---|---|---|
| Prostate Tumors | | | | |
| AT-3 | 36 | | | |
| 11095 | 50 | | | |
| 2PR121D(1)R | 70 | | | |
| Breast Tumors | | | | |
| MX-1 | 78 | | | |
| MT/W9Q-S | 45 | | | |
| 13762NF | 70 | | | |
| Colon Tumors | | | | |
| CX-1 | 31 | | | |
| CX-5 | 83 | | 54 | |

TABLE 3-continued

Response of Human and Animal Tumors to Treatment with Bombesin/Gastrin Releasing Peptide Analogues (Percent Test/Control\*)

| | BIM-26187 | BIM-26218 | BIM-26247 | BIM-26225 |
|---|---|---|---|---|
| Hepatoma | | | | |
| M5123 | 62 | 70 | | |
| M7777 | 67 | | | 52 |
| M7806 | 83 | | | |
| Lung Tumors | | | | |
| NCI-H345 | 66 | | | |
| A-549 | 63 | | | |

\Percent Test/Control was based upon tumor weight of test animals as compared to tumor weight of vehicle treated controls.
\*Analogs tested were designated as possessing tumor inhibitory activity when Percent Test/Control was < 80% T/C. A lower Percent Test/Control indicates a greater tumor inhibitory effect.

Figure 2:
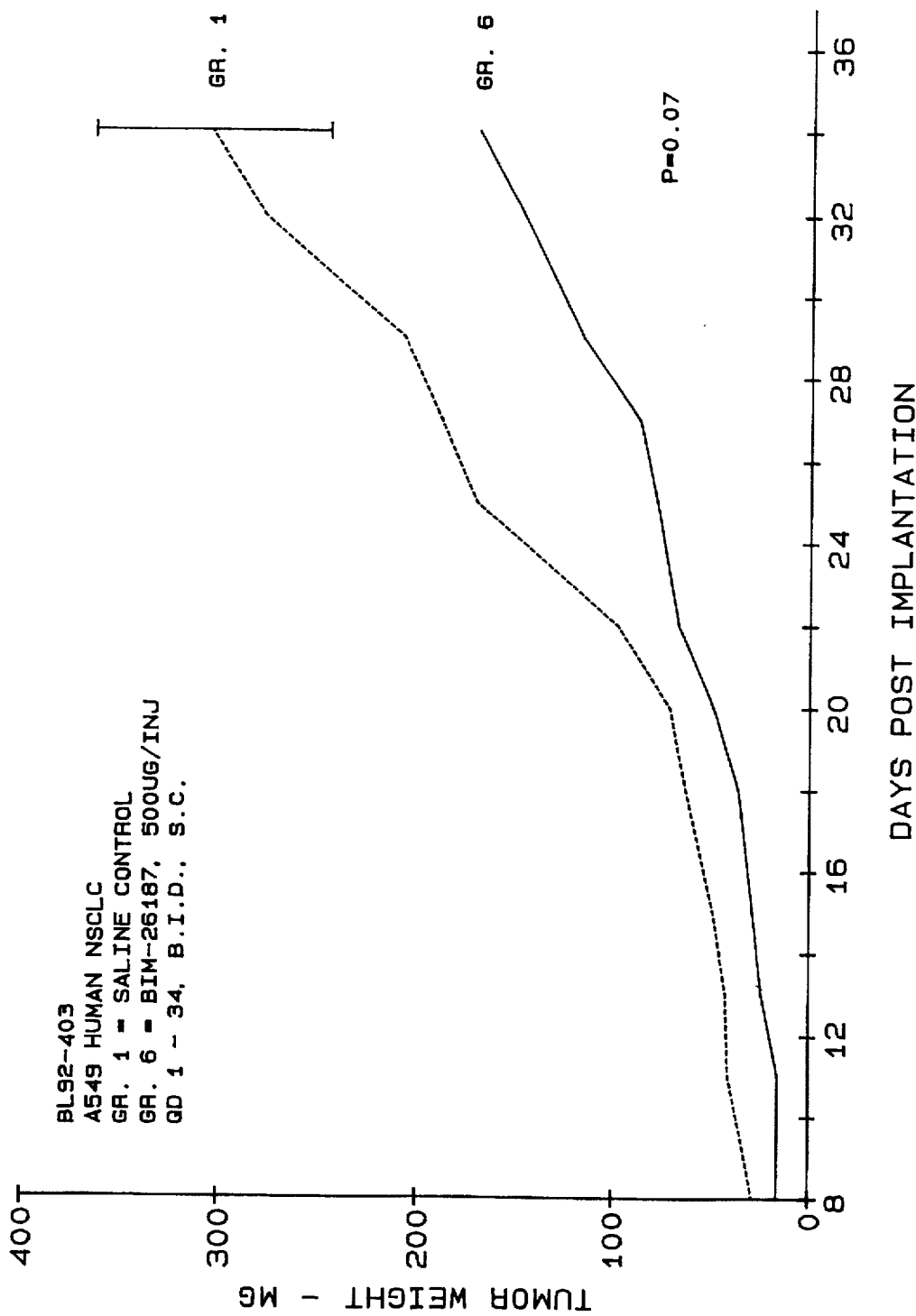

FIG. 1 and FIG. 2 show that BIM-26224 and BIM-26187 are capable of inhibiting small cell lung carcinoma ("SCLC") and non-small cell lung carcinoma ("NSCLC"), respectively. The structure of BIM-26224 is H-D-Phe-Gln-Trp-Ala-Val-Gly-His-Leu-Leu-$NH_2$. For structure of BIM-26187, see above.

USE

Analogs of the invention are useful for treating colon, prostatic, breast, pancreatic, liver cancer or lung cancer, for preventing the proliferation of smooth muscle, for suppressing appetite, for stimulating pancreatic secretion, or for suppressing a craving for alcohol. Analogs of the invention are administered to a mammal, particularly a human, in one of the traditional modes (e.g., orally, parenterally, transdermally, transmucosally, or via drug-releasing implants), in a sustained release formulation using a biodegradable biocompatible polymer, or by on-site delivery using micelles, gels and liposomes, or rectally (e.g., by suppository or enema). The analogs can be administered to a human patient in a dosage to be determined by the attending physician ranging from 0.25 mg/kg/day to 5 mg/kg/day.

Furthermore, compounds of the present invention, particularly those with Tyr at the N-terminus, can be used for diagnostic purposes and for the tumor targeting of radioisotopes such as $^{131}$Iodine.

OTHER EMBODIMENTS

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed:

1. A therapeutic peptide of the formula:

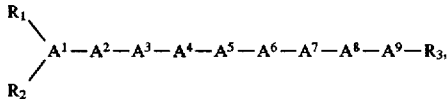

wherein:

$A^1$ is a D-isomer selected from Trp, β-Nal, Phe and p-X-Phe, where X is F, Cl, Br, $NO_2$, OH or $CH_3$;

$A^2$ is Gln;

$A^3$ is the D- or L-isomer selected from β-Nal, Trp, Phe, and p-X-Phe, where X is F, Cl, Br, $NO_2$, OH or $CH_3$;

$A^4$ is Ala, Val, Leu, Ile, Nle, or α-aminobutyric acid;

$A^5$ is Val, Ala, Leu, Ile, Nle, Thr, or α-aminobutyric acid;

$A^6$ is Gly, Sar, p-Ala, or the D-isomer selected from Ala, N-methyl-Ala, Trp, and β-Nal;

$A^7$ is His, 1-methyl-His, 3-methyl-His, or Lys;

$A^8$ is Leu, Ile, Val, Nle, a-aminobutyric acid, Trp, β-Nal, Phe, or p-X-Phe, where X is F, Cl, Br, $NO_2$, OH or $CH_3$;

$A^9$ is Met, Met-oxide, Leu, Ile, Nle, α-aminobutyric acid, or Cys;

each $R_1$ and $R_2$, independently, is H, $C_{1-12}$ alkyl, $C_{7-10}$ phenylalkyl, or $COE_1$, where $E_1$ is $C_{1-20}$ alkyl, $C_{3-20}$ alkenyl, $C_{3-20}$ alkynyl, phenyl, 3,4-dihydroxyphenylalkyl, naphthyl, or $C_{7-10}$ phenylalkyl; provided that when either $R_1$ or $R_2$ is $COE_1$, the other must be H; and $R_3$ is OH, $NH_2$, $C_{1-12}$ alkoxy, $C_{7-10}$ phenylalkoxy, $C_{11-20}$ naphthylalkoxy, $C_{1-12}$ alkylamino, $C_{7-10}$ phenylalkylamino, $C_{11-20}$ naphthylalkylamino; or a pharmaceutically acceptable salt thereof.

2. The therapeutic peptide of claim 1, wherein $A^1$ is the D-isomer selected from DOPA Phe and p-X-Phe, where X is F, Cl, Br, $NO_2$, OH or $CH_3$; $A^7$ is His, 1-methyl-His, or 3-methyl-His; $A^8$ is Leu, Ile, Val, Nle, α-aminobutyric acid, Trp, βNal, Phe, or p-X-Phe, where X is F, Cl, Br, NO2, OH or CH$_3$; and E$_1$ is C$_{1-20}$ alkyl, C$_{3-20}$ alkenyl, C$_{3-20}$ alkynyl, phenyl, naphthyl, or C$_{7-10}$ phenylalkyl.

3. The therapeutic peptide of claim 2, wherein A$^9$ is Leu, Ile, Nle, α-aminobutyric acid, or Cys.

4. The therapeutic peptide of claim 2, wherein
Al is D-Phe, D-Tyr, or D-Cpa;
A$^2$ is Gln;
A$^3$ is Trp;
A$^4$ is Ala;
A$^5$ is Val;
A$^6$ is Sar, Gly, β-Ala, or D-Ala;
A$^7$ is His;
A$^8$ is Leu, Phe, or Cys; and
A$^9$ is Met, Leu, Ile, Nle, or Cys.

5. The therapeutic peptide of claim 4 of the formula:
H-D-Phe-Gln-Trp-Ala-Val-Gly-His-Leu-Leu-NH$_2$.

6. The therapeutic peptide of claim 4 of the formula:
H-D-Phe-Gln-Trp-Ala-Val-Gly-His-Leu-Met-NH$_2$.

7. The therapeutic peptide of claim 4 of the formula:
H-D-Cpa-Gln-Trp-Ala-Val-Gly-His-Leu-Met-NH$_2$.

8. The therapeutic peptide of claim 4 of the formula:
H-D-Cpa-Gln-Trp-Ala-Val-Gly-His-Leu-Leu-NH$_2$.

9. The therapeutic peptide of claim 4 of the formula:
H-D-Phe-Gln-Trp-Ala-Val-D-Ala-His-Leu-Leu-NH$_2$.

10. The therapeutic peptide of claim 4 of the formula:
H-D-Phe-Gln-Trp-Ala-Val-D-Ala-His-Leu-Met-NH$_2$.

11. The therapeutic peptide of claim 4 of the formula:
H-D-Cpa-Gln-Trp-Ala-Val-D-Ala-His-Leu-Met-NH$_2$.

12. The therapeutic peptide of claim 4 of the formula:
H-D-Phe-Gln-Trp-Ala-Val-Gly-His-Phe-Leu-NH$_2$.

13. The therapeutic peptide of claim 4 of the formula:
H-D-Phe-Gln-Trp-Ala-Val-D-Ala-His-Phe-Met-NH$_2$.

14. The therapeutic peptide of claim 4 of the formula:
H-D-Phe-Gln-Trp-Ala-Val-D-Ala-His-Phe-Leu-NH$_2$.

15. The therapeutic peptide of claim 4 of the formula:
H-D-Phe-Gln-Trp-Ala-Val-Gly-His-Leu-Nle-NH$_2$.

16. The therapeutic peptide of claim 4 of the formula:
H-D-Phe-Gln-Trp-Ala-Val-D-Ala-His-Leu-Nle-NH$_2$.

17. The therapeutic peptide of claim 4 of the formula:
H-D-Phe-Gln-Trp-Ala-Val-Gly-His-Phe-Nle-NH$_2$.

18. The therapeutic peptide of claim 4 of the formula:
H-D-Phe-Gln-Trp-Ala-Val-D-Ala-His-Phe-Nle-NH$_2$.

19. The therapeutic peptide of claim 4 of the formula:
H-D-Phe-Gln-Trp-Ala-Val-Gly-His-Phe-Met-NH$_2$.

20. The therapeutic peptide of claim 1 of the formula:
H-D-Tyr-Gln-Trp-Ala-Val-Gly-His-Phe-Met-NH$_2$.

21. The therapeutic peptide of claim 1 of the formula:
H-D-Tyr-Gln-Trp-Ala-Val-Gly-His-Leu-Leu-NH$_2$.

22. The therapeutic peptide of claim 1 of the formula:
H-D-Tyr-Gln-Trp-Ala-Val-Gly-His-Leu-Met-NH$_2$.

23. The therapeutic peptide of claim 1 of the formula:
H-D-Tyr-Gln-Trp-Ala-Val-Gly-His-Phe-Nle-NH$_2$.

24. The therapeutic peptide of claim 1 of the formula:
H-D-Tyr-Gln-Trp-Ala-Val-Gly-His-Leu-Nle-NH$_2$.

25. The therapeutic peptide of claim 1 of the formula:
H-D-Tyr-Gln-Trp-Ala-Val-Gly-His-Phe-Leu-NH$_2$.

26. The therapeutic peptide of claim 1, wherein A$^2$ is Gln, and A$^8$ is Leu, Ile, Val, Nle, α-aminobutyric acid, Trp, βNal, Phe, or p-X-Phe, where X is F, Cl, Br, NO$_2$, OH or CH$_3$.

* * * * *